United States Patent [19]

Tashjian et al.

[11] Patent Number: 4,694,481
[45] Date of Patent: Sep. 15, 1987

[54] TRANSPORTABLE X-RAY APPARATUS

[75] Inventors: Robert J. Tashjian, West Boylston; Charles E. Moreland, Wakefield, both of Mass.

[73] Assignee: New England Institute of Comparative Medicine, West Boylston, Mass.

[21] Appl. No.: 766,132

[22] Filed: Aug. 15, 1985

[51] Int. Cl.⁴ .......................................... H05G 1/02
[52] U.S. Cl. ................................................ 378/198
[58] Field of Search ............................. 378/195–198

[56]  References Cited

U.S. PATENT DOCUMENTS

| | | |
|---|---|---|
| 1,530,063 | 3/1925 | Tichy . |
| 1,876,737 | 9/1932 | Opp . |
| 2,051,508 | 8/1936 | Wildeboer . |
| 2,319,712 | 5/1943 | Williams . |
| 2,343,846 | 3/1944 | Robinson . |
| 2,369,453 | 2/1945 | Goldfield et al. . |
| 2,831,123 | 4/1958 | Daly . |
| 3,508,059 | 4/1970 | Vanderpool . |
| 3,673,407 | 6/1972 | Wiswell . |
| 3,790,805 | 2/1974 | Foderaro . |
| 3,801,790 | 4/1974 | Gotzl et al. . |
| 3,878,394 | 4/1975 | Golden . |
| 3,902,070 | 8/1975 | Amor et al. . |
| 4,053,778 | 10/1977 | Franke . |
| 4,181,347 | 1/1980 | Clark . |
| 4,326,131 | 4/1982 | Waerve . |
| 4,387,468 | 6/1983 | Fenne et al. . |

FOREIGN PATENT DOCUMENTS

| | | | |
|---|---|---|---|
| 1213565 | 3/1966 | Fed. Rep. of Germany | ...... 378/198 |
| 201842 | 12/1982 | Japan | ................................ 378/198 |

Primary Examiner—Frederick R. Schmidt
Assistant Examiner—Steven P. Schad
Attorney, Agent, or Firm—Blodgett & Blodgett

[57]  ABSTRACT

A transportable X-ray apparatus which is adapted to be transported in a transport vehicle mounted external of the transport vehicle. The transport X-ray apparatus comprises includes an elongated vertical mast mounted on a support base, a carriage slidable mounted on the mast, and a radiation assembly which includes a collimator and a tube unit assembly. The radiation assembly is mounted on the carriage and a support assembly is mounted on a transport vehicle so that the transportable X-ray apparatus extends externally of the transport vehicle.

13 Claims, 4 Drawing Figures

TRANSPORTABLE X-RAY APPARATUS BACKGROUND OF THE INVENTION

The present invention relates generally to an X-ray apparatus and specifically to an X-ray apparatus which is transportable to a site which is remote from a clinic or hospital.

Almost all hospitals and clinics are equipped with X-ray apparatus for medical examinations. The apparatus is located in a special room which is lined with lead or other shielding material. Patients are brought to the X-ray room for examination. Considering the hazards of radiation and the bulk of the X-ray apparatus, this has been the most practical arrangement for X-ray examination. However, in many cases, it is not practical or advisable to transport a patient to an X-ray room. For example, in the case of an accident victim, it is very often ill-advised to move the victim if there is any possibility of a serious facture, particularly in the neck area or any portion of the spinal column. It would be extremely helpful to the emergency medical team to have X-ray pictures of the victim before moving the victim to determine if there is a break and to know the exact location of the break. In this way, proper precautions can be taken to prevent further injury in moving an accident victim or a patient. In a case of a large animal, it is not always practical to transport the animal to a clinic because of the animal's size or because of the nature of an injury. For example, if a horse is suspected of having a broken leg, it would be impractical or nearly impossible to transport the horse to a clinic for examination.

Portable X-ray units have been devised which can be carried to an injury site. However, these units must be small enough to be transported and, therefore, do not have sufficient power due to their small size to be effective in X-ray diagnoses. Mobile X-ray units are also known. However, these mobile X-ray units have the disadvantage that the victim has to be transported into the unit for an examination. In other words, this involves the same problems and dangers which are associated with transporting an injured animal or a accident victim to a clinic or hospital. These and other difficulties experienced with the prior art devices had been obviated by the present invention.

It is, therefore, a principal object of the invention to provide a transportable X-ray apparatus which has a high power capacity and which can be transported to a remote examination site by a motor vehicle for providing X-ray examinations of a patient at the site.

Another object of this invention is the provision of a transportable X-ray apparatus which is adapted to be transported by the motor vehicle to the remote examination site and which is adapted to be supported by an extended from the vehicle so that it can be brought to the patient without moving the patient.

A further object of the present invention is the provision of a transportable X-ray apparatus which is adjustable for taking X-ray pictures in all planes so that a full range of X-ray pictures can be taken of the patient without moving the patient.

It is another object of the present invention to provide a transportable X-ray apparatus which consists of a plurality of elements which can be attached at the examination site and detached for storing and transporting in the vehicle.

A still further object of the invention is the provision of a transportable X-ray apparatus which consists of a plurality of detachable elements in which each of the elements can be handled by a single individual.

It is a further object of the invention to provide a transportable X-ray apparatus which is highly versatile and which is easy to use.

With these and other objects in view, as will be apparent to those skilled in the art, the invention resides in the combination of parts set forth in the specification and covered by the claims appended hereto.

SUMMARY OF THE INVENTION

In general, the invention consists of a X-ray apparatus which is adapted to be transported in a motor vehicle and to be mounted externally of the vehicle. The transportable X-ray apparatus comprises a support assembly which includes a base and a vertical mast, a carriage which is mounted on the mast for sliding vertical movement, a radiation assembly which includes a collimator and a tube unit assembly, and means for mounting the radiation assembly on a carriage and for mounting the support assembly on the motor vehicle so that the transportable X-ray apparatus extends externally of the transport vehicle.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
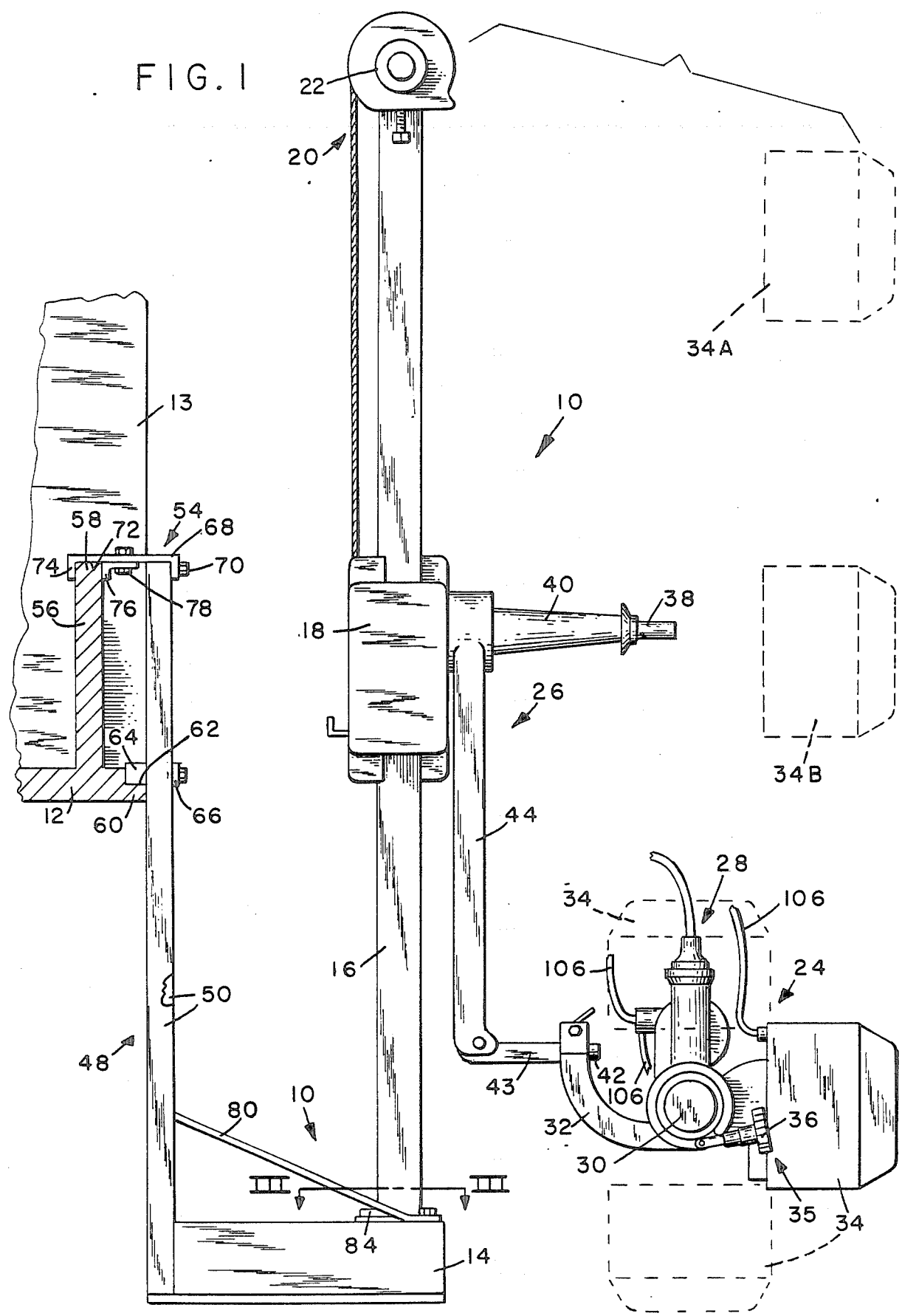
FIG. 1 is a side elevational view of a transportable X-ray apparatus embodying the principals of the present invention.
Figure 2:
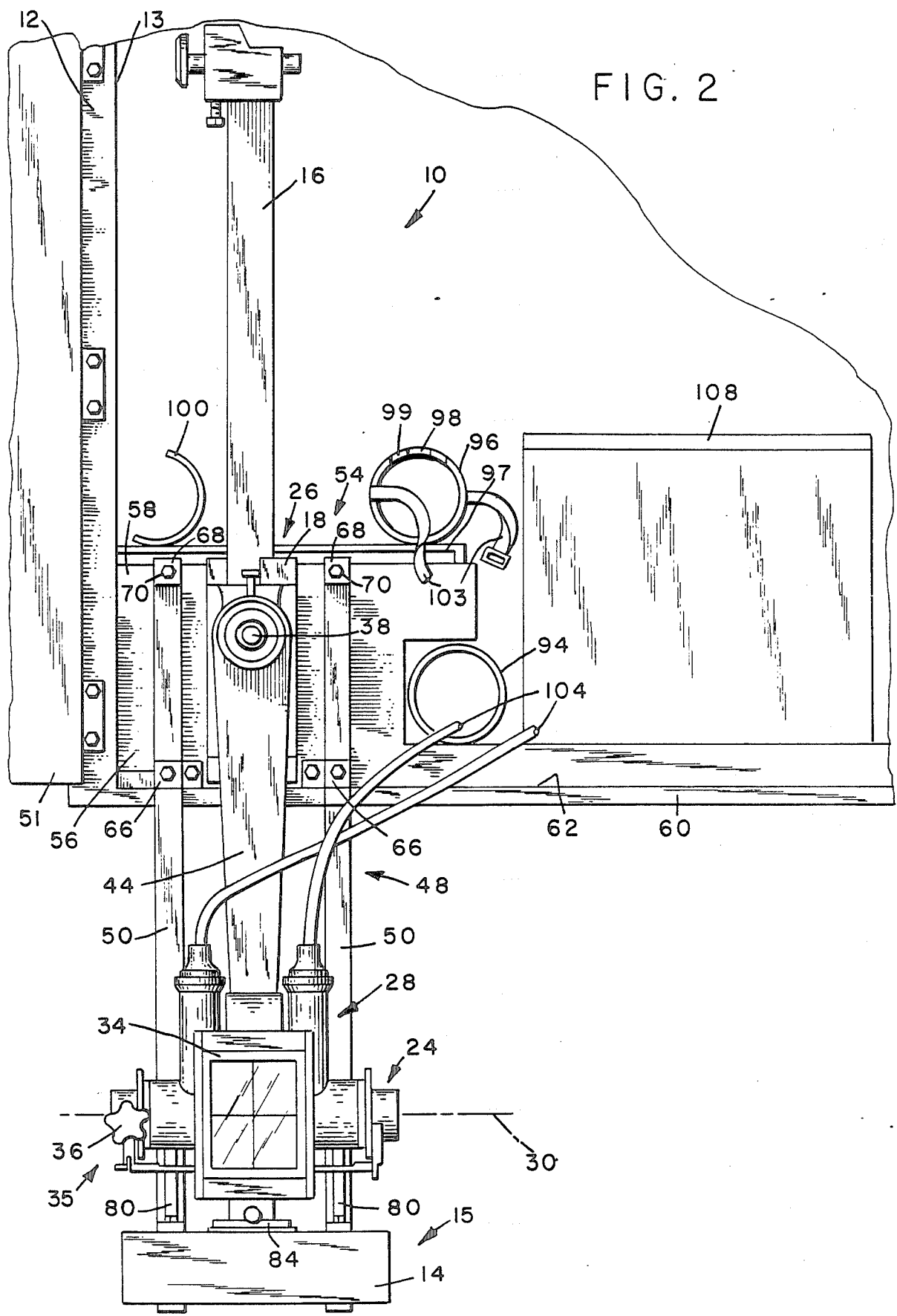
FIG. 2 is a front elevational view of the transportable X-ray apparatus.

Referring particularly to FIGS. 1 and 2 the transportable X-ray apparatus of the present invention is generally indicated by the reference numeral 10 and is shown in assembled operative position in association with a transport motor vehicle such as an ambulance 12. The transportable X-ray apparatus 10 is shown extending from a rear bay opening 13 of the ambulance 12. The X-ray apparatus 10 is fully supported by the ambulance 12 so that it is moveable with the ambulance to a specific location.

The X-ray apparatus 10 comprises: a support assembly which is generally indicated by the reference numeral 15, and a radiation assembly which is generally indicated by the reference numeral 24. First mounting means, generally indicated by the reference numeral 26, mount the radiation assembly 24 to the support assembly 15. The support assembly 15 is supported at the end of the ambulance 12 by second mounting means 48.

The support assembly 15 includes a horizontal support base 14, an elongated vertical mast 16 and a carriage 18 which is slidably mounted on the mast 16 for vertical motion relative to the mast. The carriage 18 is adjustably mounted on the mast 16 by means of a cable and pulley system generally indicated by the reference numeral 20 which is separated by a hand crank 22. The radiation assembly 24 comprises a tube unit assembly which is generally indicated by the reference numeral 28 and a collimator 34 which is removable mounted on the tube unit assembly 28. The tube unit assembly 28 includes a frame 32 and a tube housing 29 which is rotatable mounted about a horizontal axis 30 relative to the frame 32. The collimator 34 rotates with the tube housing to any desired position about the axis 30 within a 180° arc. The extreme positions of the collimator are illustrated by dotted lines in FIG. 1. Once that the tube housing and collimator have been rotated to a desired position, they are locked into that position by means of a tube lock generally indicated by the reference numeral 35, which is operated by turning a hand wheel 36. The radiation assembly 24 is of a general type which is illustrated, for example, in a maintenance and operating instructions for "X-RAY APPARATUS SET" requistion, "FSN 7610-027-2010, Manual, technical." Picker X-Ray Part Number T55-331 by Picker X-ray Corporation of Cleveland, Ohio, 1966."

The radiation assembly 24 is operatively connected to the carriage 18 by means of the first mounting means 26. The first mounting means 26 comprises a horizontal support arm 40 which is removable mounted on the carriage 18 and contains a first horizontal spindle 38. A second horizontal spindle 42 is fixed to one end of a second horizontal support arm 43 which, in turn, is fixed to the lower end of a vertical support arm 44. The upper end of the vertical support arm 44 is fixed to the horizontal support arm 40. The first horizontal spindle 38 is considerably higher than the second horizontal spindle 42 relative to the carriage 18, as shown most clearly in FIG. 1. The frame 32 of the radiation assembly 24 is adapted to be removable mounted on either of the horizontal spindles 38 and 42. The radiation assembly 24 can be rotated about the horizontal axis of either of the spindles 38 and 42. The axis of rotation on either of the spindles 38 and 42 is 180° relative to the axis 30. By mounting the frame 43 on the horizontal spindle 38 the collimator 34 can be moved from an uppermost position which is indicated by dotted lines 34A to a lower position which is approximately at the full line position of the collimator in FIG. 1. When the frame 43 is mounted on the lower horizontal spindle 42, the collimator can be moved from an upper position which is shown by the dotted lines 34B to a lower position which is not shown but which is considerably below the horizontal support base 14.

The second mounting means 48 for supporting the supporting assembly 15 at the back end of the ambulance 12 comprises a pair of vertical brackets 50 which are fixed to the rear end of the horizontal support base 14. The second mounting means 48 also includes an anchoring fixture which is generally indicated by the reference numeral 52. Anchoring fixture 52 includes a vertical abutment 56 which has a free top end 58 and a horizontal shelf 60 which has a top surface 62. The abutment 56 extends upwardly from the floor 57 of the ambulance. The horizontal shelf 60 forms the lower portion of the door jam for a rear door 51 of the ambulance. A horizontal projection or bar 64 is attached to the vertical brackets 50 by means of mounting brackets 66. An attaching fixture, generally indicated by the reference numeral, 54 comprises a pair of horizontal brackets 68 which are attached to the upper ends of the vertical brackets 50 by means of bolts 70. The rearward end of each horizontal brackets 68 is provided with a lower horizontal groove 72 which is adapted to receive the free top end 58 of the abutment 56. The groove 72 is formed by a downwardly extending lip 74 at the extreme rear end of the brackets 68 and a L-shaped bracket 76 which is adjustably mounted on the bracket 68 by means of a bolt 78. The bracket 66 enables the bar 64 to be adjusted vertically, relative to the vertical brackets 50. The adjustments which are provided by the brackets 66 and 76 enable the second mounting means 48 to compensate for variations in the sizes and relative positions of the shelf 60 and the abutment 56 from one transport motor vehicle to another. The second mounting means 48 enables the X-ray apparatus 10 to be supported at the rear end of the vehicle in cantilever fashion, so that the apparatus can be moved freely above the ground to a specific location by maneuvering the rear end of the transport vehicle toward the location. A pair of re-enforcing struts 80 extend from the vertical brackets 50 to the support base 14 to provided extra rigidity to the support assembly 15.

Figure 3:
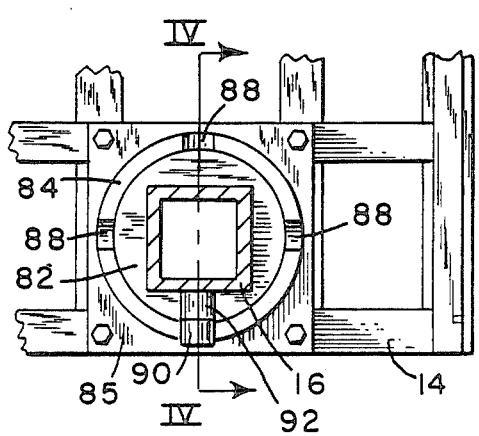
FIG. 3 is fragmentary horizontal cross-sectional view of the X-ray apparatus taken on the line III—III of FIG. 1.
Figure 4:
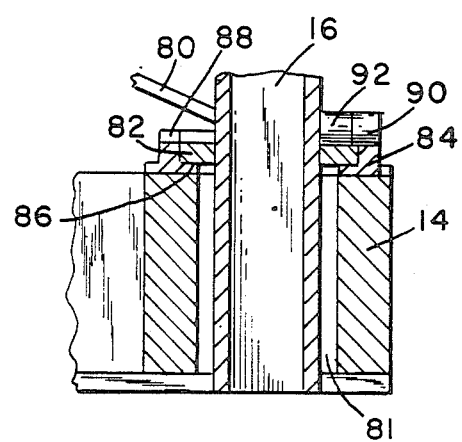
FIG. 4 is a vertical sectional view taken on the line IV—IV of FIG. 2.

The mast 16 is removable mounted on the horizontal support base and is mounted on the base 14 for rotation about a vertical axis which extends along the center of the beam. Referring particularly to FIGS. 3 and 4, the base 14 is provided with an opening 81 for receiving the lower end of the beam 16. An annular ring 82 is fixed to beam 16 at a point which is spaced from the bottom end of the tube. A ring 84 is fixed to a plate 85 which is in turn bolted to the top of the horizontal support base 14. The ring 84 has an internal annular seat 86 for receiving the annular ring 82 as shown in FIG. 4. This enables the ring 82 to rotate within the ring 84. A roller 90 is rotatable mounted on a fixture 92 which is fixed to the outer surface of the tube 16. The upper surface of the ring 84 is provided with a plurality of notches 88, for receiving the roller 90. There are four notches, for example, showin in FIG. 3. The notches 88 and the roller 90 function as detente means for locking the beams 16 in one of four set positions. The position of the beam 16 is changed by applying a torque to the beam which causes the roller 90 to roll out of one of the notches 88 and to ride along the upper surface of the ring 84 until the roller reaches the next notch. At this point, the roller drops into the next notch to retain the beam 16 in its new position.

The operation and advantages of the present invention will now be readily understood in view of the above description. Prior to be transported to an examination site, the transportable X-ray apparatus the present invention is stored in a compact package in the ambulance. The collimator is in an enclosed space with an open top which is formed, in part, by the abutment 56. The mast 16 is stored within a tube 94 which is fixed to the floor of the ambulance. The first mounting means 26 is stored within a tube 96 which is fixed to a shelf 97 which overlays the abutment 56. The tube 96 has a relatively narrow slot 98 which extends along the top of the tube for nearly its entire length for receiving the support arm 43 and the spindle 42. The end of the tube 96 which faces the rear opening 13 of the ambulance has a relatively wide slot 99 for receiving the first horizontal support arm 40. When the first mounting means 26 is stored within the tube 96 the arm 40 and the arm 43 extend above the tube 96 through the slots 99 and 98, respectively. The support assembly 15 and the second mounting means 48 are stored as a unit on top of the shelf which overlays the abutment 56. One of the brackets 50 is guided within a cradle 100 which is fixed to the shelf 102. All of the elements are secured in place by appropriate restraining means as, for example, straps 103 which are secured to the sides of the tube 96 for holding the first mounting means 26 in place within the tube 96. The tube unit assembly 28 is mounted on appropriate brackets, not shown, on one of the side walls of the ambulance. With all of the components of the transportable apparatus 10 safely stored within the ambulance, the ambulance is now ready to be driven to an examination site. When the ambulance 12 arrives at the examination site which may be the scene of an accident, a farm or a stable, the ambulance is maneuvered so that it is backed up to the approprimate point of examination. When an approximate point of examination is reached, the doors 51 are opened. The first item to be removed is the combination which includes the support assembly 15 and the second mounting means 48. The horizontal brackets 68 are attached to the abutment 56 so that the horizontal bar 64 rests on the shelf 60. The support assembly 15 is, therefore, suspended from the rear end of the truck and spaced from the ground. The mast 16 is then removed from the tube 94 and inserted to the opening 81 of the base 14 so that the ring 82 seat within the ring 84 and the mast 16 extends vertically, as shown in FIG. 1. The first mounting means 26 is removed from the tube 96 and attached to the carriage 18 so that the arm 44 extends downwardly as shown in FIG. 1. The tube unit assembly 28 is then removed from a supporting bracket on the side wall of the ambulance and mounted on either of the spindles 38 and 42. The collimator 34 is removed from its enclosure behind the abutment 56 and mounted on the tube unit assembly 28. High tension cables 104 remain connected at all times to transformer equipment, not shown, which is located in a permanent location within the ambulance. Additional electrical cables 106 are operatively connected to the transformer equipment and to a control unit 108 which remains in a permanent location at the rear end of the ambulance.

When the X-ray apparatus 10 is fully assembled as shown in FIGS. 1 and 2 it is ready for operation. The various adjusting elements of the apparatus enable the collimator 34 to assume a full range of position relative to the base 14. The two spindles 38 and 42, in combination with the vertically adjustable carriage 18, enable the collimator 34 to assume any vertical position from the upper position shown by the dotted lines 34A to a position well below the base 14. It is conceivable, for example, that a patient may be located at a point below road level in a ditch or down an embankment and can not, as a safety precaution, be moved prior to X-ray examination. The pivotal mounting of the mast 16 enables the collimator to be moved about a vertical axis which extends through the center of the beam 16. The collimator 34 can also be rotated about the horizontal axis 30 and also about the central horizontal axis of either the spindle 42 or the spindle 38. Because of its association with a motorized vehicle, such as an ambulance, the X-ray apparatus of the present invention can be brought to virtually any location which is remote from a clinic or hospital. In addition, the elements which support the X-ray components to the vehicle enable high capacity X-ray components to be used. At the same time, the detachable aspect of the X-ray components enable the entire X-ray apparatus to be assembled and disassembled by a single individual.

In the preferred embodiment of this invention, means would be provided in the vehicle to develop and to view the X-ray photographs. The developing means might be a portable wet chemical development lab. Alternatively, X-ray films of the instant-developing type, such as those sold by the Poloroid Corporation, could be used. In that case, a developing means suitable for that type of film would be provided in the vehicle.

This invention also involves the concept of transmission of the X-ray image to a remote site for examination by other personel or for storage. This concept has two basic embodiments, each involving the establishment of a communication link (wire, radio, microwave, etc.) between the vehicle and the remote site. In one version, The standard X-ray film image would be transmitted to the remote site by means of conventional facsimile equipment located in the vehicle. In a second version, a special X-ray camera would convert the X-ray transmission through the patient directly into a transmission code the could go through the communication link without the need for any X-ray film. This camera could take the form of a conventional television camera focused on a fluoroscopic screen set up to form the X-ray image. The camera might also take the form of a solid-state receptor consisting of a planar array of X-ray sensors on which the X-ray image is focused. The array would be electronically rastered to form the transmission signal.

It is obvious that minor changes may be made in the form and the construction of the invention without departing from the material spirit thereof. It is not, however, desired to confine the invention to the exact form herein shown and describe, but it is desired to include all such as properly come within the scope claimed.

The invention having been thus described, what is claimed as new and desired to secure by Letters Patent is:

1. Transportable X-ray apparatus which is adapted to be transported in a motor vehicle and to be mounted externally on the transport vehicle, said transportable X-ray apparatus comprising:
    (a) a support assembly which includes a horizontal support base and an elongated vertical mast,
    (b) a carriage which is mounted on the mast for sliding vertical movement,
    (c) a radiation assembly which includes a collimator and a tube unit assembly which is operatively connected to the collimator,
    (d) first mounting means for supporting said radiation assembly on said carriage for vertical movement with the carriage, and
    (e) second mounting means for supporting said support assembly on the transport vehicle so that the transportable X-ray apparatus extends externally of the transport vehicle, said second mounting means comprising:
        (1) a vertical bracket which is fixed to said horizontal support base and which has a free top end,
        (2) an anchoring fixture at one end of the vehicle, and
        (3) an attaching fixture which is fixed to said vertical bracket for operatively engaging said anchoring fixture so that the entire transportable X-ray apparatus is suspended from said anchoring fixture.

2. Transportable X-ray apparatus as recited in claim 1, wherein said anchoring fixture comprises:
    (a) a vertical abutment which has a free top end,
    (b) and a horizontal shelf which has a top surface, said shelf being located outwardly of said vertical abutment and below the free top ends of said vertical bracket and said vertical abutment.

3. Transportable X-ray apparatus as recited in claim 2, wherein said attaching fixture comprises:
   (a) a horizontal projection which is fixed to said vertical bracket and which is adapted to rest on the top surface of said shelf for supporting the weight of said transportable X-ray apparatus, and
   (b) a horizontal bracket which is operatively connected to said abutment and said vertical bracket above said shelf for preventing relative horizontal movement between the top end of said vertical bracket and the top end of said abutment.

4. Transportable X-ray apparatus as recited in claim 3, wherein one end of said horizontal bracket is fixed to the top end of said vertical bracket and the opposite end of said horizontal bracket has a groove which is adapted to receive the free top end of said abutment.

5. Transportable X-ray apparatus as recited in claim 3, wherein said projection is vertically adjustably mounted on said vertical bracket.

6. Transportable X-ray apparatus as recited in claim 3, wherein said motor vehicle has a rear opening and a floor, said abutment extending upwardly from said floor adjacent said rear opening and said shelf being located at the rear end of said cargo floor between said abutment and said rear opening.

7. Transportable X-ray apparatus as recited in claim 1, wherein said vertical mast is removably mounted in said base 8. Transportable X-ray apparatus as recited in claim 7, wherein said mast has a free bottom end and said base is provided with a vertical socket for receiving said bottom end.

9. Transportable X-ray apparatus as recited in claim 8, wherein the bottom end of said mast is mounted in said vertical socket for rotation about a vertical axis.

10. Transportable X-ray apparatus which is adapted to be transported in a motor vehicle and to be mounted externally on the transport vehicle, said transportable X-ray apparatus comprising:
    (a) a support assembly which includes a horizontal support base and an elongated vertical mast,
    (b) a carriage which is mounted on the mast for sliding vertical movement,
    (c) a radiation assembly which includes a collimator and a tube unit assembly which is operatively connected to the collimator,
    (d) first mounting means for supporting said radiation assembly on said carriage for vertical movement with the carriage, said first mounting means comprising: p2 (1) a first horizontal spindle which is mounted on said carriage and which is adapted to suport said radiation assembly so that said radiation assembly is removably mounted on said first spindle, and
    (2) a second horizontal spindle which is supported on said carriage and which is vertically spaced from said first horizontal spindle, said second horizontal spindle being adapted to support said radiation assembly so that said radiation assembly is removable mounted on said second spindle, and
    (e) second mounting means for supporting said support assembly on the transport vehicle so that the transportable X-ray apparatus extends externally of the transport vehicle.

11. Transportable X-ray apparatus as recited in claim 10, wherein said first mounting means comprises:
    (a) a horizontal support arm, one end of said support arm being fixed to said carriage and the opposite end of said support arm supporting said first horizontal spindle,
    (b) a vertical support arm, one end of said vertical support arm being fixed to said horizontal support arm and the opposite end of said vertical support arm supporting said second horizontal spindle.

12. Transportable X-ray apparatus as recited in claim 10, wherein said radiation assembly comprises:
    (a) a frame which is adapted for mounting on either of said first and second spindle for rotation about a horizontal axis, and
    (b) a horizontal shaft which is supported on said frame, the central longitudinal axis of said shaft extending at a right angle to the central longitudinal axis of said first and second spindles, said collimator and said tube unit being mounted on said shaft for rotation relative to said frame.

13. Transportable X-ray apparatus as recited in claim 12, wherein said collimator is detachable mounted on said tube unit assembly so that said collimator and said tube unit assembly rotate as a unit about said shaft.

* * * * *